(12) United States Patent
DeLeo et al.

(10) Patent No.: US 6,413,976 B1
(45) Date of Patent: Jul. 2, 2002

(54) COMPOSITIONS AND METHOD FOR DECREASING NEUROPATHIC PAIN

(75) Inventors: Joyce A. DeLeo, Lebanon, NH (US); Peter Schubert, Apfeldorf (DE)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/958,291

(22) PCT Filed: Mar. 14, 2000

(86) PCT No.: PCT/US00/06548
§ 371 (c)(1),
(2), (4) Date: Feb. 4, 2002

(87) PCT Pub. No.: WO00/71128
PCT Pub. Date: Nov. 30, 2000

Related U.S. Application Data

(60) Provisional application No. 60/128,005, filed on Apr. 6, 1999.

(51) Int. Cl.[7] .............................................. A61K 31/52
(52) U.S. Cl. ........................ 514/263; 514/264; 514/265; 514/866
(58) Field of Search ................................ 514/263, 264, 514/265, 866

(56) References Cited

U.S. PATENT DOCUMENTS 5,475,002 A    12/1995    Danielisova ................. 514/263

OTHER PUBLICATIONS

Kamada et al., *No To Shinkei*, 1996, 48, 1022–1028.
Kwon et al., *Arch. Pharm. Res.*, 1998, 21, 698–702.
Mielke et al., *Alzheimer Dis. Assoc. Disord.*, 1998, 12, S29–35.
Miki et al., *Clin. Ther.*, 1991, 13, 747–753.
Rother et al., *Dement. Geriatr. Cogn. Disord.*, 1998, 9, 36–43.

*Primary Examiner*—Frederick Krass
(74) *Attorney, Agent, or Firm*—Licata & Tyrrell P.C.

(57) ABSTRACT

Compositions containing propentofylline, and methods for treating neuropathic pain with such compositions, are disclosed.

1 Claim, No Drawings

COMPOSITIONS AND METHOD FOR DECREASING NEUROPATHIC PAIN

The application is a 371 of PCT/US00/06548, filed Mar. 14, 2000 and claims the benefit of U.S. Provisional Application No. 60/128,005, filed Apr. 6, 1999.

INTRODUCTION

This invention was supported in part by funds from the U.S. government (National Institutes of Health Grant No. DA 11276) and the U.S. government may therefore have certain rights in the invention.

BACKGROUND OF THE INVENTION

Propentofylline is a xanthine derivative that has been tested extensively in humans as a neuroprotective agent for treatment of Alzheimer's Disease and vascular dementia. In clinical trials, propentofylline has been shown to be both safe and effective for the treatment of these neurodegenerative diseases (Mielke et al., Alzheimer Dis. Assoc. Disord., 1998, 12, S29–35; Rother et al., Dement. Geriatr. Cogn. Disord., 1998, 9, 36–43). The effects observed with propentofylline treatment include a reduction in the extent of brain neuropathology, an improvement in cognitive function, a decrease in activation of microglia, and inhibition of inflammatory processes. The drug is well absorbed and extensively metabolized following oral dosing (Kwon et al., Arch. Pharm. Res., 1998, 21, 698–702). The pharmacokinetic and pharmacodynamic profile of propentofylline have made it a promising therapeutic in the treatment of neurodegenerative diseases.

The pharmacological effects of propentofylline have been linked to inhibition of adenosine transport and inhibition of phosphodiesterase. Studies have also suggested this drug has effects to stimulate the synthesis and secretion of nerve growth factor, and can act as a transcriptional modulator and inducer of apoptosis in certain types of brain cells (Kamada et al., No To Shinkei, 1996, 48, 1022–1028). Propentofylline has also been shown to have a differential effect on the production of certain cytokines such as interleukin-6, interleukin-1 beta, and tumor necrosis factor alpha (Miki et al., Clin. Ther., 1991, 13, 747–753).

Chronic pain from nerve injury is a debilitating condition that affects millions of Americans. Such pain can occur as a result of cancer, multiple sclerosis, HIV-associated neuropathy, diabetic neuropathy, trigeminal neuralgia, postherpetic neuralgia (shingles), phantom limb pain, nerve injury due to trauma or surgery, and deafferentation pain. Most of these chronic pain syndromes are refractory to standard analgesics such as morphine and non-steroidal anti-inflammatory drugs. In addition, such drugs must be given in high doses such that they are associated with a variety of side effects that often limits the long-term use. Many of these side effects are life-threatening such as kidney toxicity and gastrointestinal distress in the case of the non-steroidal anti-inflammatory drugs and respiratory depression in the case of morphine. Clearly, there is a need to identify new compounds for treatment of chronic pain, in particular ones with a better therapeutic index (ratio of effective dose to toxic dose).

It has now been found that propentofylline, a drug shown to have a favorable safety profile in humans with neurodegenerative disease, has unexpected effects to decrease chronic neuropathic pain.

SUMMARY OF THE INVENTION

The present invention is a pharmaceutical composition containing propentofylline and methods for decreasing neuropathic pain.

DETAILED DESCRIPTION OF THE INVENTION

Neuropathic pain, or chronic pain from nerve injury, is not only chronic and intractable, but debilitating, often causing severe physical, psychological and social distress. It has been found that propentofylline, a safe and effective drug for treatment of neurodegenerative diseases such as Alzheimer's Disease, has a previously unrecognized effect to reduce chronic nerve pain.

Experiments were performed using a well-established animal model for chronic pain, spinal nerve transection in the rat. The model measures changes in mechanical allodynia, or an increased sensitivity following non-noxious stimulus, such as touch. Rats were injected intraperitdneally one day before and then daily for ten days following nerve transection. Results showed that there was a significant decrease in mechanical allodynia following treatment with propentofylline at doses of 1 and 10 mg/kg. The effect was dose-dependent, with larger reductions seen with higher doses of the drug.

The same model. was used with rats injected intrathecally with either saline or propentofylline (1 or 3 $\mu$g), daily for 10 days. Again, there was a significant decrease in mechanical allodynia following treatment with propentofylline. The responses were also dose-dependent with the largest reduction seen at the highest dose tested.

These data demonstrate the efficacy of propentofylline to decrease neuropathic pain after both peripheral and central administration. As expected, the dose required to produce a reduction in pain responses in the animal was lower with central administration. In a preferred embodiment, propentofylline would be administered to an animal, including a human. The pain could be due to a variety of causes including but not limited to cancer, multiple sclerosis, low back pain associated with radiculopathy (root injury), HIV-associated neuropathy, diabetic neuropathy, trigeminal neuralgia, postherpetic neuralgia, phantom limb pain, or nerve injury due to surgery or trauma. The drug would be administered in a pharmaceutically acceptable carrier either orally, intravenously, intramuscularly, subcutaneously, by infusion pump implanted subcutaneously, intrathecally, or any other applicable route of administration that would deliver the drug to the desired site of action. One of skill would understand how to formulate and deliver propentofylline based on knowledge of the pharmacokinetics of the drug collected in patients treated for neurodegenerative diseases and the clinical studies that supported the development of the drug for neurodegenerative diseases. Propentofylline's effects on chronic nerve pain will also be useful for designing studies to elucidate the mechanisms of chronic pain and potentially in the design of other novel compounds for treatment of chronic nerve pain.

The following non-limiting examples are provided to further illustrate the instant invention.

EXAMPLES

Example 1

Rat Model for Chronic Neuropathic Pain

Surgery was performed under inhalation anesthesia using halothane in 100% oxygen at 4% and maintained at 2%. Each rat received a single unilateral lesion directed at a left L5 spinal root or spinal nerve. The nerve was identified, freed from adjacent nerves and transected. For sham lesions, a minilaminectomy was performed of the L5 vertebral segment without lesioning. Animals were allowed to recover from anesthesia and were not subjected to any additional surgical procedures or anesthesia until the end of the study when they were euthanized.

Propentofylline was injected intraperitoneally at doses of 1 and 10 mg/kg the day before and for each day of testing (10 days). Saline injections served as a control. Other rats were injected intrathecally at doses of 1 and 3 μg on each day of testing.

Example 2

Behavioral Testing for Sensitivity to Pain

Mechanical hypersensitivity was measured as the frequency of foot withdrawals elicited by a defined mechanical stimulus. Each rat, under unrestrained conditions, was placed beneath an inverted, ventilated Plexiglas cage upon an elevated aluminum screen surface with 1 cm mesh openings. Animals had been previously (before surgery) acclimated to the environment and the experimenter.

In blinded testing, rats were subjected to sequential series of 10 tactile stimulations to the plantar surface of the ipsilateral hindpaw using 2 and 12 gauge von Frey filaments (Stoelting Co., WoodDale, Ill.) sequentially. The lateral half of the underside of the paw, excluding the toes, heel, and lateral edge of the foot was tested. Efforts were made to vary the stimulus test spot on the foot. Mechanical sensitivity was assessed by recording the total number of responses elicited during three successive trials separated by at least 10 minutes.

Results showed that there were dose-dependent decreases in responses to stimulation in this test with increasing doses of propentofylline, regardless of the route of administration (both central and peripheral routes).

What is claimed is:

1. A method for treating neuropathic pain, comprising administering to an animal suffering from neuropathic pain a pharmaceutical composition comprising an effective amount of propentofylline.

* * * * *